United States Patent [19]

Schnepp-Pesch et al.

[11] Patent Number: 5,158,564

[45] Date of Patent: Oct. 27, 1992

[54] ATHERECTOMY APPARATUS

[75] Inventors: Wolfram Schnepp-Pesch, Ettlingen; Josef Lindenberg, Karlsruhe, both of Fed. Rep. of Germany

[73] Assignee: Angiomed AG, Karlsruhe, Fed. Rep. of Germany

[21] Appl. No.: 551,013

[22] Filed: Jul. 11, 1990

[30] Foreign Application Priority Data

Feb. 14, 1990 [DE] Fed. Rep. of Germany ....... 4004507
Apr. 7, 1990 [DE] Fed. Rep. of Germany ... 9004074[U]

[51] Int. Cl.⁵ .............................................. A61B 17/32
[52] U.S. Cl. ..................................... 606/159; 606/169
[58] Field of Search ............... 606/180, 170, 159, 128, 606/127, 169; 604/22

[56] References Cited

U.S. PATENT DOCUMENTS

| | | | |
|---|---|---|---|
| 2,816,552 | 12/1957 | Hoffman | 606/159 |
| 3,320,957 | 5/1967 | Sokolik | 606/180 |
| 4,650,466 | 3/1987 | Luther | 604/105 X |
| 4,771,774 | 9/1988 | Simpson et al. | 606/171 |
| 4,885,003 | 12/1989 | Hillstead | 604/22 |
| 4,886,061 | 12/1989 | Fischell et al. | 604/22 X |
| 4,890,611 | 1/1990 | Monfort et al. | 606/159 |
| 4,895,560 | 1/1990 | Papantonakos | 606/159 X |
| 4,966,604 | 10/1990 | Reiss | 606/180 X |
| 5,030,201 | 7/1991 | Palestrant | 604/22 |

Primary Examiner—Michael H. Thaler
Attorney, Agent, or Firm—Antonelli, Terry, Stout & Kraus

[57] ABSTRACT

An apparatus for atherectomy comprising at least one rotatable member for removing deposits, coatings, occlusions, etc. in a vessel, with the at least one rotary member being radially expandable from a paraxial position.

1 Claim, 6 Drawing Sheets

ATHERECTOMY APPARATUS

Field of the Invention

The invention relates to an atherectomy apparatus with at least one rotary member for removing deposits, coatings, occlusions, ect. in a vessel.

Background of the Invention

An atherectomy apparatus is known, which has, at the proximal end of a driving shaft constructed as a helically wound wire, two cutting blades directed conically towards one another. In view of the lack of clarity existing regarding the terms proximal and distal, as the parts of an extremity located towards the trunk or heart are called "proximal", the end of the inventive apparatus towards the heart or a part thereof is referred to as proximal and the part directed towards the surgeon or doctor as distal.

In the known apparatus the distal area of the cutting edges has a considerable diameter as a result of the conical tapering towards the proximal end and the shaft has a corresponding diameter. As the shaft must be guided through a catheter, the catheter must have an even larger diameter. Thus, the canal to be created through a stenosis or a closure in a vessel to be created with the known apparatus determines the size of the puncture point for inserting the apparatus, which must have a much larger cross-section than the canal to be exposed in the vessel. The shaft formed by the helical winding of a wire is difficult to seal as a result of its thickness, so that blood can pass out of the vessel and out of the apparatus at the distal end. In the case of stronger clamping of a sealing valve, the friction is increased to such an extent that the driving shaft can be damaged.

Further on deposits, such as thrombotic occlusions in vessels or the like may be removed by a rotary element moved in the vessel towards the closing or constriction and with respect to which a rotational speed of about 100,000 r.p.m. has been proposed in order to pulverize the occlusion material. However, there is a risk of the pulverized particles being redeposited at other points and possibly in much narrower, but important vessels, where damage can be caused. Other apparatus rotating at a lower speed up to max 500 r.p.m. merely move the vessel-closing material to the side. Thus, it is not possible to achieve a reliable, permanent exposure of a stenosis, quite apart from an opening of an occlusion. In addition, apparatuses are known, which cut out constricting material in the vessel in one way or another. To the extent that a rotary catheter is used, the danger exists that it takes the vessel wall with it during its rotation with the associated risk of an entaglement, so that here again it is only possible to operate at very low speeds. To the extent that the removal takes place by working instruments passed through a catheter on a shaft, then the instruments must operate at a distance from the catheter orifice, so that possibly the suction exerted by the catheter will not be adequate for removing all the abraded particles.

Summary of the invention

The aim underlying the invention essentially resides in providing an improved atherectomy apparatus while obviating the aforementioned disadvantages.

Another object of the invention is to safely move abraded parts of occlusion towards the catheter orifice, so that they can be reliably suctioned off by an applied vacuum.

According to the invention by an athetectomy apparatus, is characterized in that the rotary member is radially expandable or spreadable from a paraxial position. In preferred manner the cutting edge or edges extend substantially axially in the paraxial position.

Through the provision of radially spreadable or expandable members for the removal by abrasion of the coatings, deposits, ect., it is possible to initially insert the same in a contracted position into the vessel, so that a function with a small cross-section is required. At the operating point the members can be radially expanded, so that it is possible to carry out an atherectomy with an exposed canal in the vessel and which has a much larger cross-section than the necessary function point. This reduces stress on the patient. Working with the inventive apparatus is also made easier.

The members can fundamentally be placed outwards in their cutting or operating position by a spreading member. In this case the widening process of the vasoconstriction is carried out from the proximal end thereof and the members and initially moved in the contracted apparatus through a conventionally formed canal before they are radially expanded. Fundamentally the same procedure can be carried out, but is not necessary, in a construction in which the end areas of the members can be axially moved towards one another. In this case the members are constructed in an elastically flexible manner and are radially expanded in that with axial spacing points located on in each case one member are axially moved towards one another, so that the preferably wire-like members are bend radially outwards. This construction has the advantage that there are no outwardly extending free faces or ends of the members.

According to a preferred construction, the axial fixing of the members is brought about in that the members are constructed on support parts, which are held together with the spacing of reciprocally arranged joining points and the latter are axially movable towards one another. Over a portion of the wire parts, the members preferably have cutting edges or knives formed by grinding. The cutting edges are essentially directed in the tangential direction of a solid of revolution formed by the wire parts. Fixing can take place in that a taut wire is passed through the joining points and, as a result, the the joining points can be drawn towards one another. In addition, the wire parts can be held together by sleeves in the vicinity of the joining points.

According to further developments, the expandable members are connected at the distal end with a helically wound hollow wire and at the proximal end the members or wire portions are followed by the helically wound hollow wire attachment. The distal hollow wire forms a driving shaft for the rotation of the cutting edges. While the expandable members or wire parts on which are optionally formed cutting edges are constructed separate from the hollow wire portions and can be fixed thereto in an appropriate manner, e.g. by soldering, clamping, etc., according to a preferred development the members or wire portions are constructed in one piece with the hollow wire parts.

The hollow wire attachment arranged in proximal with respect to the members, prior to the widening of the vascular lumen, contributes to creating a recanalization, in order to be able to carry out the widening and removal process by the members from the proximal end of the stenosis.

If, according to a further preferred development, the taut wire projects at the proximal end over the members or individual wires and to its projecting end is fixed a widened abutment to counteract a tensile force exerted at the distal end and the abutment is constructed as a ball or sphere, then, by pulling on the taut wire, in the distal direction the abutment can transfer the tensile force to the proximal joining or connecting area of the individual wires optionally carrying cutting edges. Thus, said connecting area can be drawn towards the distal connecting area of the individual wires, so that the latter can be positioned radially towards the outside, optionally with their cutting edges.

While the recanalization can be performed in known manner, according to a preferred development the inventive apparatus can be used for this purpose, so that it is possible to avoid repeatedly inserting and removing different instruments through the guidance catheter. For this purpose the ball formed by the taut wire extending through the proximal hollow wire portion or, in more general terms, an abutment is provided with cutting parts. The latter can be formed by diamond chips applied to the ball, but cutting edges milled out from the same or a cutting foil fixed thereto.

According to a further development, the taut wire is constructed as a hollow wire and its cavity optionally extends through the abutment.

In such a case it is possible to provide a conventional guide wire, which is used for the introduction of the inventive apparatus. Apart from an antegrade shelling out of the vessel, this in particular assists a retrograde exposure.

According to another development the apparatus or expandable members is constructed in a forceps-like manner. This gives a particularly simple construction if the cutting edges are the partly ground axial edges of the forceps jaws.

The invention further provides a drive for an apparatus for removing deposits, such as occlusions in vessels or the like, with a device for receiving the start of an elongated, hollow guide part, such as a catheter, and with a rotary connecting part to the rotary drive of devices for removing deposits upstream of the proximal end of the guide part, which is characterized in that the connecting part can be moved backwards and forwards in the axial direction relative to the guide part receptacle.

As a result of the axially movable construction of the connecting part for the working instruments used for the abrading removal of the deposits and which can have different constructions, it is possible to introduce the instruments for the removal of the material from the catheter orifice in the vicinity of the stenosis or occlusion and, while maintaining the rotation, to rhythmically return the said instruments to the catheter orifice and possibly partly into the same, so that particles carried along with the working instruments can be suctioned off by the vacuum exerted in the catheter or in the hollow guide part.

The working instruments driven by the drive can be constructed in different ways. The working instruments can be in the form of spiral or basket-shaped constructions, in which the abrading elements are in the form of blunt or tapered wires positioned axially on the circumference of a fictional spheroid. These two constructions collect the material removed in the area resulting from the abrading wires or the screw or helix construction and can reliably carry the same during their return movement to the orifice of the hollow guide part, so that the abrading material is reliably suctioned off. However, fundamentally other constructions of the instruments are possible.

The axial reciprocating movement of the connecting part of the inventive drive and therefore the working instruments connected thereto takes place manually in a preferred construction and advantageously the rotary connecting part is manually axially reciprocatable. Thus, the surgeon can control and set in a desired manner the axial reciprocating movement of the working instruments. Alternatively, in order to make the work of the surgeon easier, the rotary connecting part can be axially reciprocated by a motor drive. The axial drive can be constructed in such a way that a sleeve is provided, which is axially fixed, but connected in rotary manner to the connecting part and in non-rotary manner to the drive casing and having a closed groove passed in meander-like manner around the circumference and in which engages the cam of a transmission part rotating at a lower angular velocity than that of the connecting part. The reciprocating movement can be derived from the same motor, which brings about the high-speed rotary movement of some 100 to 2000 r.p.m. of the connecting part and therefore the working instruments, in that between the driven shaft of the motor and the transformation gear for transforming a rotary drive into the linear reciprocating movement, a transmission gear is provided, such as are e.g. known in connection with clockworks.

For the connection of the working instruments via a shaft projecting through the guide part, the connecting part can have a coupling member, e.g. in the form of a Luer-Lok or the like. The hollow, elongated guide part, in particular a catheter is firmly connected to the drive in that on the reception means for the same is constructed in the axial direction an inwardly directed circumferential groove bounded on both sides by shoulders and into which can be inserted the radial flange parts of the catheter or elements firmly connected thereto. The drive preferably has an electric motor and, in order to ensure independence from the mains and also for safety reasons, is provided with its own power storage means. The latter can be a chargeable accumulator or a battery. It is in both cases advantageous for the display means to be a LCD. Thus, the surgeon's attention is, in good time drawn, to the fact that the power supply of the power storage means is inadequate or that the voltage has dropped, so that he can replace the means in good time instead of being surprised by this phenomenon during an operation. The accumulator is preferably interchangeably arranged in a corresponding compartment in the casing. According to another preferred embodiment, the drive is provided with a speed regulator. It obviously also has an on/off switch.

BRIEF DESCRIPTION OF THE DRAWINGS

Further advantages and features of the invention can be gathered from the claims and the following description of non-limitative embodiments of the invention and with reference to the attached drawings, wherein

DETAILED DESCRIPTION

Figure 1:
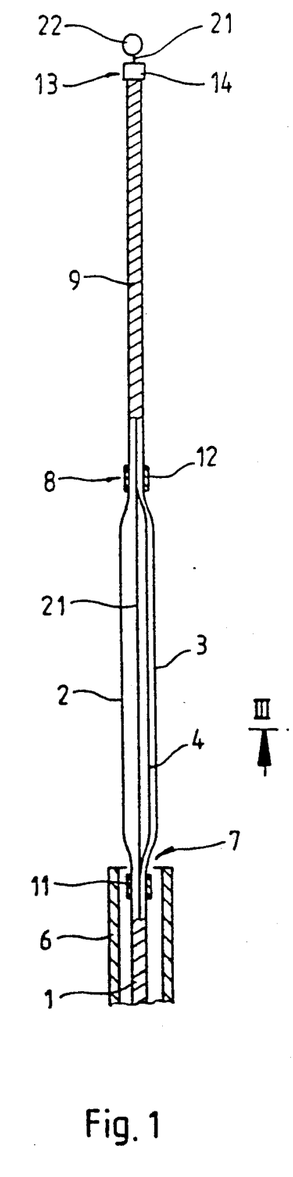
FIG. 1 is a partial sectional side view of a cutting edge of an apparatus constructed in accordance with the present invention, with the apparatus in an inserted state.

In the illustrated embodiment the inventive apparatus has a flexible hollow wire 1, which is e.g. formed by helically winding three strands 2,3,4. The hollow wire 4 is guided by a catheter 6. In a joining area 7, the helical winding of the individual wires 2,3,4 is removed and they are axially guided substantially parallel to one another until they are again brought together in a further joining area 8, which is spaced from the first area and a further portion 9 of the hollow wire 1 is formed. On the joining points 7,8 can be mounted sleeves 11,12, which prevent an untwisting of the wound areas. A sleeve 14 can also be fixed to the hollow wire 1 at the proximal end 13.

A taut wire 21 extends through the entire hollow wire 1 freely and axially thereto. The end of the taut wire 21 projecting out of the proximal end 13 of the hollow wire attachment 9 is provided with an abutment in the form of a ball or sphere 22, whose diameter is at least over the internal diameter of the attachment 9 and preferably corresponds to or is greater than the external diameter of said hollow wire attachment 9 or the sleeve 14. The ball 22 or a corresponding, optionally conically shaped abutment can be provided with cutting edges, which are either formed directly on the ball, by diamond chips or the like applied, or by a foil provided with micro-cutting edges. Particularly in the latter case the abutment is preferably constructed as a cone or cylinder.

Figures 2, 3:
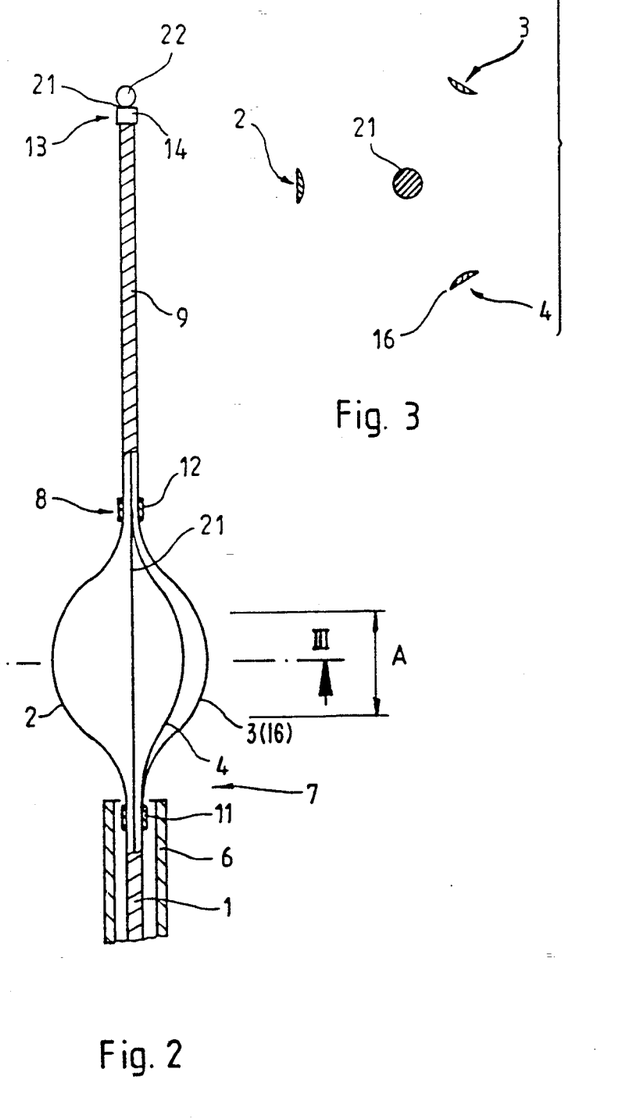
FIG. 2 is a partial cross-sectional side view of the apparatus of FIG. 1 in a working state.
FIG. 3 is a cross-sectional view taken along the line III—III in FIG. 2.
Figure 3A:
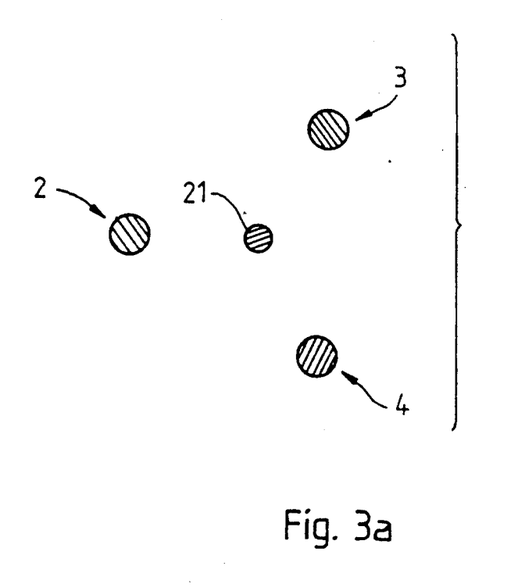
FIG. 3a is a cross-sectional view corresponding to FIG. 3 with blunt basket wires.

The individual wires 2,3,4 extending freely between the areas 7,8 are at least in the central part of their longitudinal extension A provided with cutting edges 16. The cutting edges 16 are substantially tangential to the central taut wire 21 or a spheroid formed by the wires 2,3,4. They can be formed by one side of each wire and if only one rotation direction is provided it is in the latter. However, they are preferably formed on two sides, so that the inventive apparatus can be used with two rotation directions. Considered radially (towards the wire 21 or the solid of revolution), the cutting edges 16 are as far as possible towards the outside, as shown in FIG. 3. Alternatively the wires 2,3,4 of the basket or cage formed by them must have no cutting edges and can instead be blunt, e.g. formed from round wire, as shown in FIG. 3a.

If the wires 2 to 4 with their cutting edge areas 16 in the unloaded position shown in FIG. 1, in which they only surround a small cross-sectional surface are introduced through the catheter 6 into the vicinity of a stenosis of a vessel, optionally following recanalization, then an atherectomy can be carried out, in that the taut wire 21 is drawn in the distal direction from the distal end of the apparatus. The wires 2 to 4 are axially loaded and their ends are axially pressed against one another, so that the central areas of the wires are pressed towards the outside. By rotating the wires 2 to 4, optionally by a motor, preferably battery or accumulator-operated drive acting on the distal end of the hollow wire 1, deposits in the vicinity of the stenosis can be abraded away by the cutting edges 16 and, in this way, the vessel can be largely freed again, in that the radius of the spheroid formed by the wires 2 to 4 is stepwise or continuously widened to the desired circumference. In particular, freeing or exposure can take place up to a cross-section, which is over the cross-section of the insertion catheter 6. As a result of the inventive apparatus and despite the very small function points of approximately 5 Charrière (5/3 ≈ approx. 1.7 mm) vessels up to a diameter of over 10 Charrière and in part up to 8 mm can be freed.

The recanalization of an optionally completely closed stenosis can take place in per se known manner. Instead of this if the part 22, such as a ball is provided with cutting members, the means according to the invention can be advanced in front of the stenosis and the taut wire 21 can then serve as a guidance wire. The taut wire 21 is then rotated, so that the ball 22 or the like can recanalize the stenosis and can therefore create a passage through the same. Preferably, the entire means, including the freely extending wire areas 2 to 4 can be passed through the stenosis and by drawing rearwards the wires 2 to 4 the aforementioned widening effect can be obtained.

The scaled off plaque material is preferably suctioned off through the catheter 6 and, as shown in FIGS. 1 and 2, this can take place alongside the hollow wire 1. It is also possible to use a catheter with two orifices and it is possible to inject through the secondary orifice streptokinase or the like for the partial dissolving of deposits.

Figure 4:
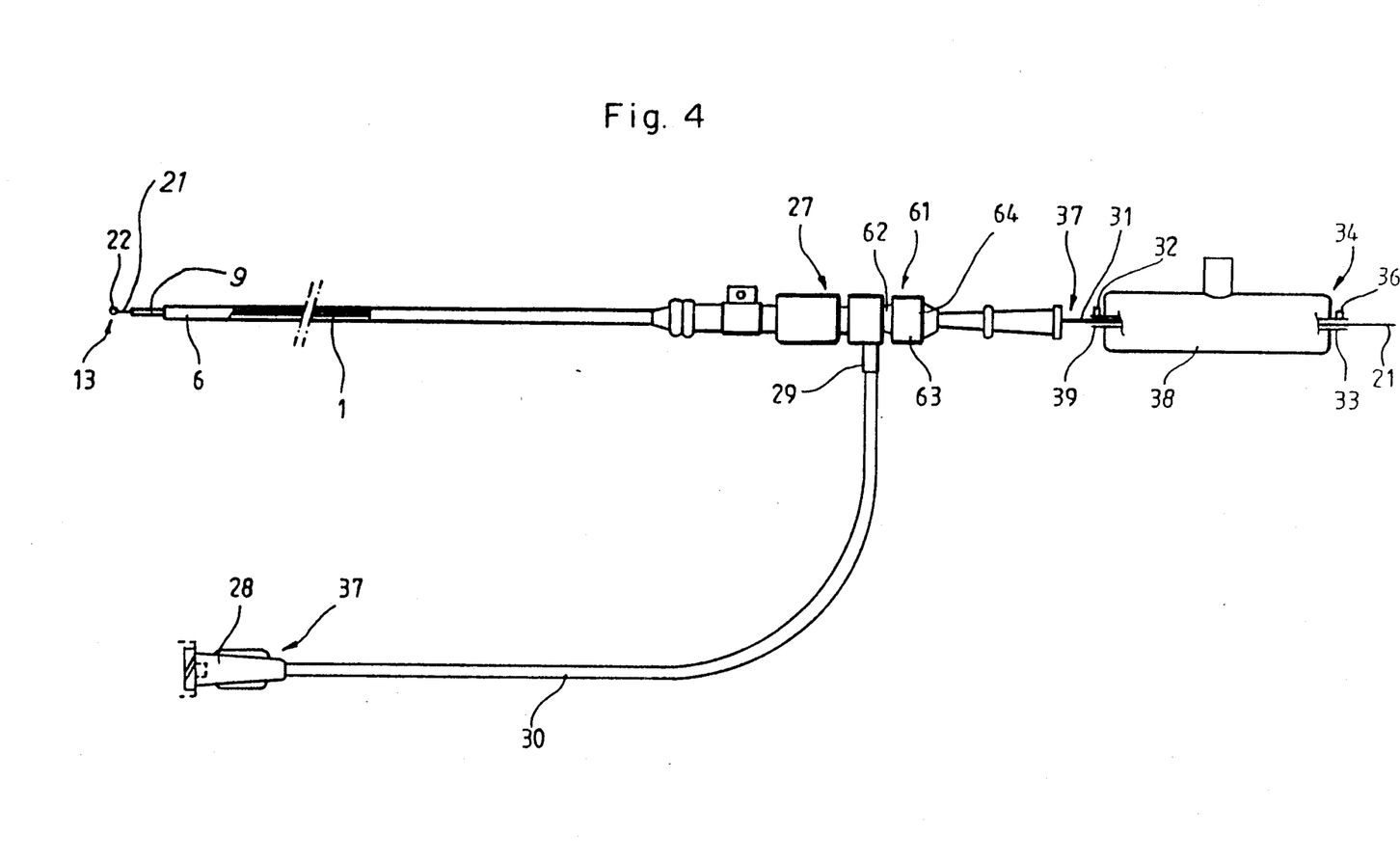
FIG. 4 is a schematic view of the apparatus of the present invention with a driving means.

A catheter arrangement 6, as can be used in the invention, is shown in FIG. 4. The catheter 6 has in its distal area 27 a branch 29, to which is fixed a hose portion 30. Its end 37 remote from the branch 29 can be connected by an adaptor 28 to a suction means, in order to suctioned off through the catheter 6 the broken off deposits. According to a preferred development the suction means is a motor, particularly electric and, preferably, battery-operated pump, whose suction rate can be varied, controlled or regulated.

A tight passage for the wires 1, 21 is provided on the proximal side of the branch 29. The seal is preferably constructed in such a way that in a valve part 61, such as a hemostatic valve, is provided a short, elastic, flexible hose part, whose diameter in the unloaded state is such that the hollow wire 1 and also the taut wire 21 with its ball 22 can be freely passed through the hose part. A sleeve attachment 62 is provided with a thread and on it is placed an internally threaded cap 63. When the cap 63 is threaded on in a direction towards the branch 29 it axially compresses the hose part by a face 64 thereof. Therefore, the hose part engages on the hollow wire 1 and forms a reliable seal. The hollow wire 1 can be axially moved backwards and forwards under friction. A distal end 31 of the hollow wire 1 is axially displaceable in a driven hollow shaft 39 of a drive motor 38, but can be braced to the shaft in non-rotary axial manner, e.g. by a bracing mechanism 32. The hollow shaft 39 is mounted so as to rotate in the motor part 38. Either shaft 39 or another hollow shaft 33 projects out of the rear end 35 of the motor 38. Through the hollow shafts 39, 33 extends the taut wire 21, which is connected in non-rotary manner to the shaft 33 by a clamping mechanism 36, whereby the shaft can be constructed in one piece with the shaft 39. After inserting the inventive means into the vessel to be exposed or freed, together with the ball 22 or the like, the motor 38 is switched on, so that the taut wire 21 and optionally also the hollow wire 1 and, in particular, the optionally roughened ball 22 connected to the taut wire 21 is rotated. By operating the motor 38, the ball 22 is moved in the proximal direction with its cutting action brought about by the rotation and is forced through the closure until a recanalization has been brought about. The hollow wire 1 with its front hollow wire attachment 9 and the individual wire portions 2 to 4 can be moved through the canal to the proximal side of the stenosis. The clamping mechanism 38 can then be released. The taut wire 21 is then drawn back, so that there is a relative displacement of wire 21 with respect to the hollow wire 1. By the ball 22, the taut wire 21 takes the hollow wire attachment 9 with it, so that the individual wires 2, 3 and 4 provided with cutting edges 16 are forced radially outwards. After obtaining a desired radius, the clamping mechanism 36 is refixed and subsequently the motor 38 is operated, so that the basket, formed by the wires 2 to 4 is rotated and, accompanied by the drawing back of the motor 38 and therefore the two wires 1 and 21, a desired hollow cylinder is cut out of the stenosis.

This process can optionally be repeated several times until the desired diameter in the vessel is obtained.

Figure 5:
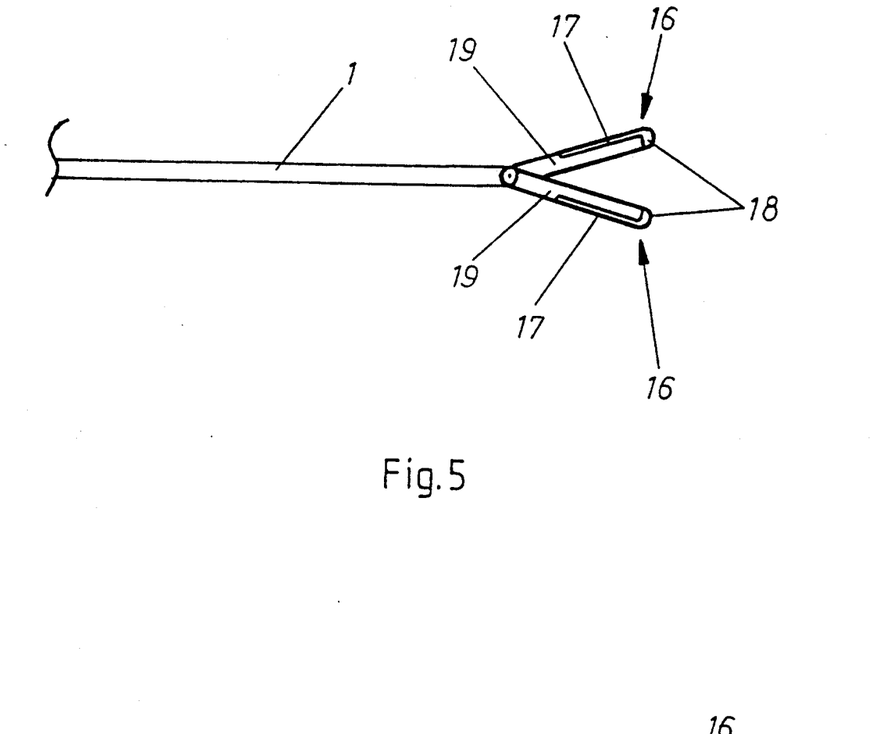
FIG. 5 is a schematic view of a forceps-like construction of the apparatus constructed in accordance with the present invention.

In the embodiment of, FIG. 5 on the proximal end of the hollow wire 1 is placed a forceps-like device, which is controllable by a wire or the like located in the interior of the hollow wire 1 for the purpose of opening and closing the forceps. In the simplified representation according to FIG. 5 the forceps have two forcep jaws 19 with cutting edges 16. In this construction the outer edges of the jaws 19 are ground and form the outer cutting edges 17. In addition, the front edges of the jaws 19 are ground for forming the front cutting edges 18.

This apparatus is preferably used in such a manner that, in the closed state, the forceps are advanced through the insertion catheter 6 up to the stenosis. The forceps are rotated by the hollow wire 1 and in the case of a further advance by the latter, the front cutting edges 18 can penetrate the stenosis. The forcep is then expanded to the desired diameter in known manner, e.g. controlled by the taut wire 21 and then drawn back, accompanied by rotation. The stenosis is then shelled out to the set diameter by the outer cutting edges 17.

Figure 6:
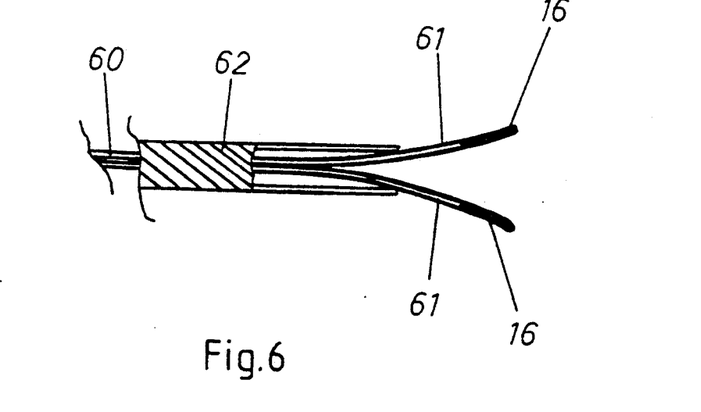
FIG. 6 is a partial cross-sectional view of another embodiment of the present invention.

FIG. 6 shows another embodiment, which is based on a type of Silverman needle 60, which has two ends 61 with cutting edges 16. The two ends 61 have an internal tension, so that they spread or expand to the extent made possible by the displaceable sleeve 62. The sleeve 62 can be connected to or be integral with the hollow wire 1 and the needle 60 can be rotated by the inner wire otherwise used as the taut wire 21 if it is connected in non-rotary manner to the needle 60. By a relative axial displacement of the sleeve 62 with respect to the needle 60, the ends 61 expand as a result of their inherent tension to the desired diameter and, in accordance with FIG. 5, by means of the cutting edges 16 it is possible to hollow out a stenosis by rotating the needle 60 and drawing forwards and backwards the needle 60 and the sleeve 62.

The inventive drive 1' according as shown in FIGS. 7-10 has a casing 2', which houses an electric motor and a power supply, such as a battery or an accumulator and which can be inserted in the casing through opening 4'. The casing also contains a speed regulator for the motor, which is controllable by a setting knob 6', so that the speed can be set and adjusted in desired ranges, e.g. between 0 and 2,000 r.p.m. or higher. The casing also contains a display 7', in this case a LCD, which shows the amount of power of the power supply means which has been consumed and therefore when a replacemnent is necessary. The drive 1' is also provided with an on/-off switch for switching the rotary drive on and off. On the front of the drive 1' a holding bridge 9' is provided on the casing 2' and at its end 11' remote from the latter, has an opening 12' which is open from the top with undercut, lateral grooves 13' and into which are insertable the radial flanges on a hollow guide part, such as a suction catheter, so that the latter can be fixed relative to the drive 1' and, in particular, its casing 2', more especially in the axial direction.

Figure 7:
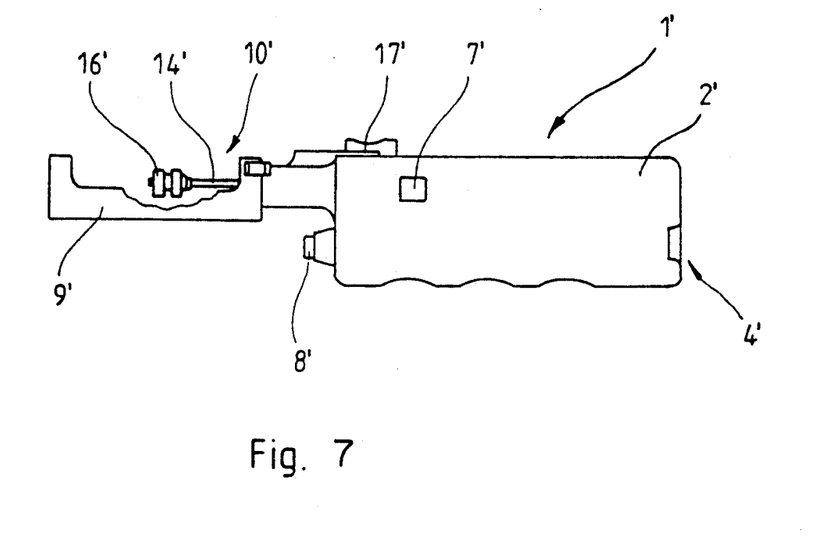
FIG. 7 is a schematic side view of the drive of the present invention.
Figure 8:
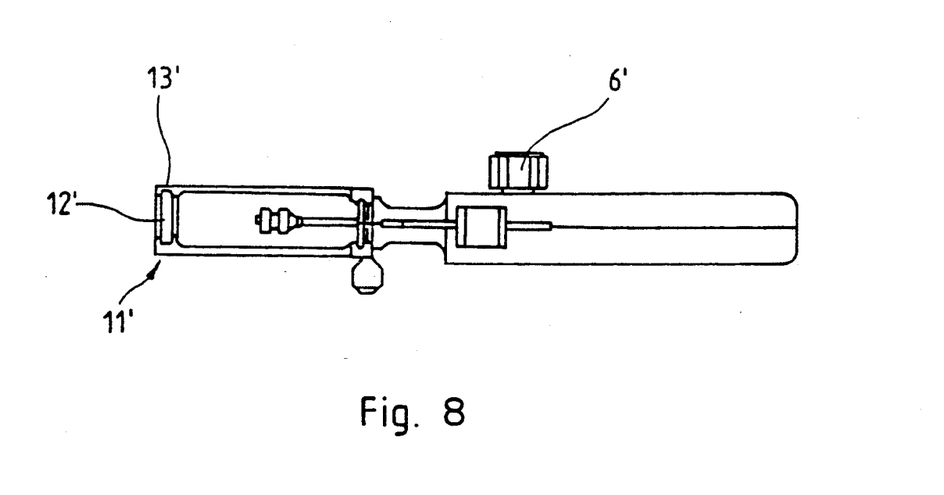
FIG. 8 is a plan view of the drive means of the apparatus of FIG. 1.

Into the space surrounded by the catheter holding bridge 9' projects a connecting part 10' with a driving shaft 14', which is provided at its free end with a connecting attachment 16', such as e.g. a male Luer-Lok. By the female Luer-Lok part can be connected in non-rotary manner a device for removing deposits by the rotation thereof, such as a rotational spiral. The device has over its length roughly corresponding to that of the hollow guide part or catheter a straight shaft and can be provided at its proximal end, i.e. the end remote from the drive 1', with a helical construction, as well as following onto the latter a ball with or without a cutting edge means, or with a radially spreadable basket-like member, optionally with a cutting edge means.

On the top of the casing is provided a slide part 17', to which is connected the shaft 14' so as to be rotatable, but axially fixed with respect thereto. The shaft 14' is once again in axial, but non-rotary engagement with a driven stub of the motor located in the casing 2'.

Figure 9:
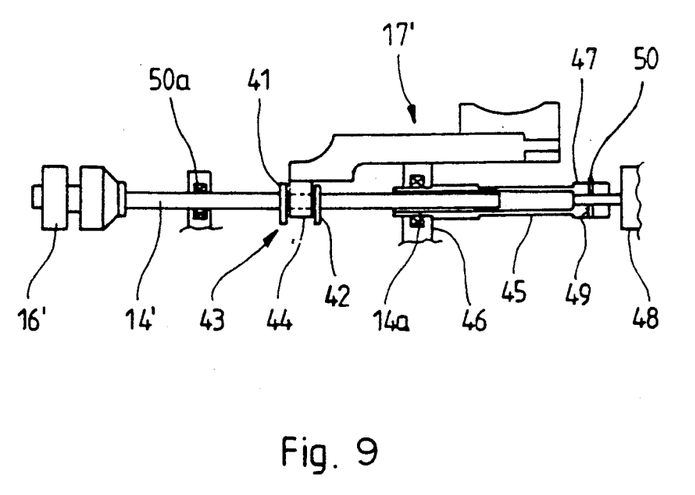
FIG. 9 is a schematic view of a coupling of a linear drive to a medium-speed rotary drive.

A specific embodiment of this connection is shown in FIG. 9. The driving shaft 14' carries at its front end in non-rotary manner the Luer-Lok 16'. It also has non-rotary radial flanges 41, 42 which are spaced from one another and which can e.g. be constructed on an engaged sleeve 43, such as a brass sleeve soldered to the shaft 14'. A C-shaped part 44 engages between the flanges 41, 42 on the shaft 14' or the sleeve 43 connected thereto, whilst ensuring rotation. This part 44 is snapped over the shaft 14' or the sleeve 43 and is firmly connected to the slide part and is e.g. constructed in one piece therewith.

On the other side of the flanges 41, 42 the shaft 14' projects into a guide sleeve 45, which is mounted in rotary manner relative to the casing by a bearing 46. At the end of the guide sleeve the driven shaft 47 of a motor 48 projects into the sleeve 45 and is connected in non-rotary manner thereto by a pin 50 passing through transverse bores 49. The cross-section of the part 14a of shaft 14' projecting into the guide sleeve 45, as well as the internal cross-section of sleeve 45 are not circular, but instead have a shape differing from the circular, e.g.

flattened, so that the shaft 14' can also be rotated by the guide sleeve 45 driven by the motor 48. The shaft 14' is also guided by a bearing 50a with respect to which it is displaceable and rotatable.

As a result of the described construction the rotary drive of the shaft 14' by the motor 48 and the axial displaceability of the shaft 14' relative to and in the sleeve 45 are ensured.

Figure 10:
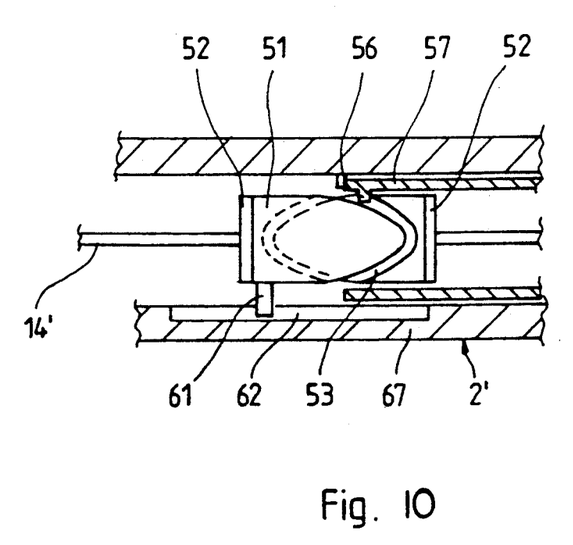
FIG. 10 is a schematic cross-sectional view of an embodiment for a motor reciprocating linear drive of a connecting part.

FIG. 10 diagrammatically shows an embodiment for transforming the linear reciprocating movement derived from the rotary drive for the connecting part. The connecting part is rotatable, but is axially fixed to a sleeve 51, similar to sleeve 43, e.g. by radial flanges 52 firmly engaging on the connecting part on either side of the sleeve 51. In order to reduce friction, it is possible to provide within the sleeve 51 between the latter and the connecting part 14a a conventional bearing means. In the outer circumference of the sleeve is provided a closed groove, which passes in meander-like manner from one face of the sleeve and then around the same and back to the first face. The cam 56 of a further sleeve 57 engages in the groove. So that the sleeve 51 does not rotate with the sleeve 57, it is guided by a cam 61 in a groove 62 of the wall 63 of the casing 2 or a part firmly connected thereto. During the rotation of the sleeve 57 the cam 56 is urged against the wall of the groove 53 of the sleeve 51 inclined with respect to its rotation direction. As the sleeve cannot rotate with it due to its linear guide 61, 62, it is axially displaced by the cam 56 until the latter arrives at one of the reversal points of the groove 53 at the faces of sleeve 51, where the linear movement is then reversed. By the flanges 52 the sleeve 51 takes the connecting part with it during its reciprocating movement. The rotary drive of the rotary sleeve 57 can be derived from the rotary drive of the motor and, as the reciprocating movement of the sleeve 51 and, therefore, the rotary movement of the sleeve 57 is much smaller than the rotary movement of the motor, by a reduction gear, which can e.g. be constructed in the form of a sun gear-planet gear with an annular gear constructed in the sleeve 57, in the form of a clockwork motions or the like. The rotary drive of the shaft 14' and therefore the connecting part 10' takes place in the same way to that which has been described relative to FIG. 9.

We claim:

1. An apparatus for atherectomy, the apparatus comprising:

a catheter;

a hollow wire guided by said catheter, said hollow wire including at least one rotary member for removing at least one of deposits, coatings and occlusions in a vessel;

a first helically wound hollow wire attachment provided on a proximal end of said at least one rotary member, and a second helically wound hollow attachment provided on a distal end of said at least one rotary member;

a taut wire extending through said first and second helically wound attachments and said rotary member;

means provided on a proximal end of said taut wire and cooperable with a proximal end of said first helically wound hollow wire attachment for enabling a radial expansion of said at least one rotary member from a paraxial position upon drawing the taut wire in a distal direction of the apparatus;

a drive for the apparatus including means for receiving said catheter, and rotary connecting means for connecting a rotary drive for the at least one rotary member, wherein the rotary connecting means is axially reciprocatable relative to the catheter by a motor; and a sleeve firmly and rotatably connected to the rotary connecting means and in a non-rotary manner to a drive casing, said sleeve having a closed meandering groove guided around a circumference engageable with a cam of a transmission part rotating at a lower angular velocity than an angular velocity of the rotary connecting means.

* * * * *